(12) United States Patent
Levy et al.

(10) Patent No.: US 8,618,242 B2
(45) Date of Patent: Dec. 31, 2013

(54) PHOTO-ACTIVATED ATTACHMENT OF CHOLESTEROL TO POLYURETHANE SURFACES FOR ADHESION OF ENDOTHELIAL CELLS

(75) Inventors: Robert J. Levy, Merion Station, PA (US); Ivan Alferiev, Clementon, NJ (US); Stanley J. Stachelek, Philadelphia, PA (US)

(73) Assignee: The Children's Hospital of Philadelphia, Philadelphia, PA (US)

( * ) Notice: Subject to any disclaimer, the term of this patent is extended or adjusted under 35 U.S.C. 154(b) by 76 days.

(21) Appl. No.: 13/263,244

(22) PCT Filed: Apr. 9, 2010

(86) PCT No.: PCT/US2010/030517
§ 371 (c)(1),
(2), (4) Date: Dec. 27, 2011

(87) PCT Pub. No.: WO2010/118306
PCT Pub. Date: Oct. 14, 2010

(65) Prior Publication Data
US 2012/0089222 A1  Apr. 12, 2012

Related U.S. Application Data (60) Provisional application No. 61/167,993, filed on Apr. 9, 2009.

(51) Int. Cl.
*C08G 64/00* (2006.01)
*C08G 63/02* (2006.01)

(52) U.S. Cl.
USPC .......................................... 528/380; 528/422

(58) Field of Classification Search
USPC .................................. 528/380, 422
See application file for complete search history.

(56) References Cited

U.S. PATENT DOCUMENTS

| 4,001,016 A | 1/1977 | Rosenkranz et al. |
| 6,497,868 B1 | 12/2002 | Tanahashi |

(Continued)

OTHER PUBLICATIONS

Chorny, et al., Michael, "Adenoviral Gene Vector Tethering to Nanoparticle Surfaces Results in Receptor-Independent Cell Entry and Increased Transgene Expression," *Molecular Therapy*, 14(3): 382-391, Sep. 2006.

(Continued)

*Primary Examiner* — Terressa Boykin
(74) *Attorney, Agent, or Firm* — RatnerPrestia

(57) ABSTRACT

A polymer is provided according to structure I

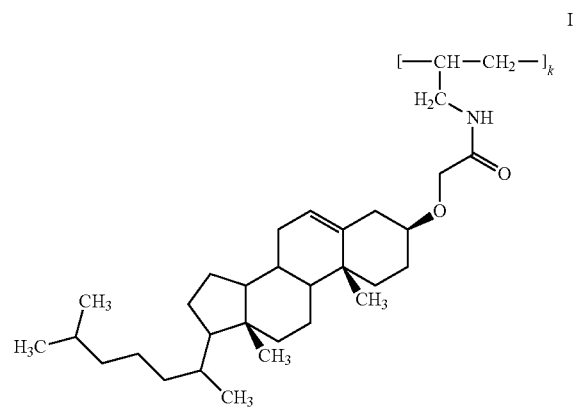

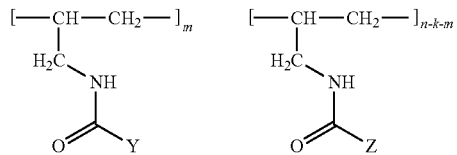

wherein Y is a thiol-reactive group and Z is an ionogenic group. The surface of a polymeric substrate is modified by contacting the surface with a polymer according to structure II or structure III and exposing the surface to ultraviolet light, optionally followed by contacting the modified surface with the polymer according to structure I.

-continued

-continued

III

15 Claims, 3 Drawing Sheets

(56) References Cited

U.S. PATENT DOCUMENTS

| | | |
|---|---|---|
| 7,408,014 B2 | 8/2008 | Levy et al. |
| 7,635,734 B2 | 12/2009 | Alferiev et al. |
| 2006/0063894 A1 | 3/2006 | Alferiev et al. |
| 2006/0147413 A1 | 7/2006 | Alferiev et al. |
| 2006/0182975 A1 | 8/2006 | Burbank et al. |
| 2009/0010984 A1 | 1/2009 | Levy et al. |

OTHER PUBLICATIONS

Stachelek, et al., Stanley J., "Cholesterol-derivatized polyurethane: Characterization and endothelial cell adhesion," *Wiley Periodicals, Inc.* 2004, pp. 200-212.

Stachelek, et al., Stanley J., "Cholesterol-Modified Polyurethane Valve Cusps Demonstrate Blood Outgrowth Endothelial Cell Adhesion Post-Seeding in Vitro and In Vivo," *Ann. Thorac. Surg.*, 81;47-55, 2006.

Young, Lee W., International Search Report dated May 19, 2010.

Lindner, Nora, International Preliminary Report on Patentability dated Oct. 11, 2011.

Amos, et al., R.A., "Biomaterial Surface Modification Using Photochemical Coupling Technology," *Encyclopedic Handbook of Biomaterials and Bioengineering, Part A: Materials*, pp. 895-926, 1995.

Koch, Troels, "Photochemical Immobilization of Anthraquinone Conjugated Oligonucleotides and PCR Amplicons on Solid Surfaces," *Bioconjugate Chem.*, 2000, 11:474-483.

Maruyama et al., Kazuhiro, "Relative Rate of Hydrogen Abstraction by the Triplet State of Phenanthraquinone," *Bulletin of the Chemical Society of Japan*, 42:3357-3359, 1969.

European Patent Office Communication dated May 15, 2013 for Appl. No. 10 762 486.8 1303.

PHOTO-ACTIVATED ATTACHMENT OF CHOLESTEROL TO POLYURETHANE SURFACES FOR ADHESION OF ENDOTHELIAL CELLS

This application is the national phase filing of International Appln. No. PCT/US2010/030517, filed 9 Apr. 2010 and claims priority of U.S. Provisional Application No. 61/167,993, filed 9 Apr. 2009, the entireties of which applications are incorporated herein by reference.

BACKGROUND OF THE INVENTION

Heart valve disease affects millions, and at this time can only be treated by valve replacement or repair surgery. Cardiac valve prostheses have not significantly improved in decades, and one problem is a progressive decline in performance of heart valve replacements over 10 to 15 years after implant, necessitating additional surgery or resulting in morbidity and mortality. Additionally, valve prostheses prepared from polymeric materials, typically polyurethanes, have limited ability to bond to the living tissue to which they are attached. Therefore, methods of providing replacement valves having good longevity in vivo, including effective attachment to living tissues, would be of considerable medical value.

SUMMARY OF THE INVENTION

In one aspect, the invention provides a polymer according to structure I wherein Y is a thiol-reactive group selected from one or more of the following moieties and Z is an ionogenic group selected from one or more of the following moieties and wherein n is an integer and k, m and n-k-m are each non-zero fractions of n.

In another aspect, the invention provides a method of modifying the surface of a polymeric substrate. The method includes contacting the surface of the polymeric substrate with a polymer according to structure II and/or a polymer according to structure III -continued wherein n is an integer and k, m and n-k-m are each non-zero fractions of n; and exposing the surface to ultraviolet light.

In yet another aspect, the invention provides a polymer according to structure III

III wherein n is an integer and k, m and n-k-m are each non-zero fractions of n.

DETAILED DESCRIPTION OF THE INVENTION

The invention provides methods and compositions for modifying the surface of a polymeric material, including especially a polyurethane substrate, to facilitate subsequent autologous endothelial seeding on the surface of the substrate. Suitable uses of such include, for example, heart valve prostheses for use as mitral valve replacements. Earlier work in this area provided polyurethane materials bearing cholesterol substituents throughout the polymer, formed by activating a pre-formed polyurethane via bromoalkylation and then contacting the activated polyurethane with a mercapto-functionalized cholesterol to functionalize the polymer. See Stachelek et al., Cholesterol-derivatized polyurethane: characterization and endothelial cell adhesion, J Biomed Mater Res A 2005, 72:200-212 and Stachelek et al., Cholesterol-modified polyurethane valve cusps show endothelial adhesion in vitro and in vivo, Ann Thorac Surg, 2006, 81:47-55, both of which documents are incorporated herein by reference.

The inventors have found, however, that while this approach does provide a surface that bears cholesterol groups, the resulting bulk functionalization is typically detrimental to the physical properties of the polymer over time, resulting in performance degradation. The inventors now disclose a method of cholesterol-modifying only the surface of already formed polymeric substrates, such as polyurethane films used in prosthetic heart valve leaflets. The surface modification involves a two-step sequence. In the first step, a multipoint photo-reactive polymeric cross-linker is irradiated on the surface of the polyurethane to provide (after reduction of dithio groups as described below) a stable thiolated surface bearing multiple thiol groups. The thiolated surface is then treated with a cholesterol-bearing thiol-reactive polymer to covalently bind cholesterol groups to the thiolated polyurethane surface. These steps will now be detailed, using polyurethane as an exemplary substrate for ease of explanation. It is to be understood, however, that the invention encompasses treatment of other polymeric substrates as well.

Polyurethane Surface Thiolation

In the first step, a polyurethane surface is modified with a polymeric photo-reactive cross-linker PBPC (Scheme A), which can be made according to the methods described in U.S. Pub. No. 2006/0147413, the entirety of which is incorporated herein by reference.

Scheme A. Surface modification of ANGIOFLEX™ (polyurethane) with SH groups

TCEP = tris(2-carboxyethyl)phosphine

The value of n is typically at least 50, and typically at most 2000 or at most 1000. The inventors have used two commercially available variants of PAA in the synthesis of PBPC: one with n≈100 and another with n≈500, and values within this range are the ones most typically used for purposes of the invention. The values of k, m and n-k-m are each non-zero fractions of n. Values of k generally will be in a range from 0.1n to 0.3n, and for m the range will typically be from 0.3n to 0.6n. Generally, k is about 0.2n and m is about 0.4n.

Although the examples herein describe modification of polyurethanes, many types of polymer can be modified with PBPC or PBPC-A (described later herein), and subsequently modified with CPB polymers, using the methods of this invention. The presence of C—H bonds in polyvinylchloride, polyethylene, polystyrene, polyesters, polyamides, etc. make them suitable for surface modification. The UV-initiated photochemical reaction of aromatic ketones (including benzophenone derivatives and anthraquinone derivatives) with almost any kind of substrate possessing C—H bonds is known to form covalent C—C bonds between the substrate and the excited ketone.

In certain applications, such as heart valves, polyurethanes are commonly used. Any polyurethane can be modified according to the invention, and one exemplary polyurethane is sold under the trade name ANGIOFLEX™, a polyether polyurethane used in the Abiomed trileaflet heart valve (supplied by Abiomed, Danvers, Mass.). Polyurethane substrates such as ANGIOFLEX™ have abundant C—H bonds capable of participation in the benzophenone crosslinking reactions involving the surface of ANGIOFLEX™ films.

Scheme B. Photo-reaction of benzophenone derivatives with C—H substrates

Without wishing to be bound by any particular theory or explanation, the inventors believe that under photolysis conditions the PBPC modifies the ANGIOFLEX™ (or other polymer) surface with covalently bound pyridyldithio (PDT) groups via grafting of the PBPC to the surface. The latter can then be cleaved with a suitable reducing agent, such as TCEP, to form thiol groups (Scheme A). Thiol functionalization can be performed analogously with PBPC-A, an anthraquinone-based analog of PBPC described later herein, and combinations of PBPC and PBPC-A may also be used.

Cholesterol-Bearing Thiol-Reactive Polymers

To attach cholesteryl residues to the thiolated ANGIOFLEX™ surface, the inventors synthesized several types of polyallylamine-based tri-functional, water-soluble, thiol-reactive polymers with cholesteryl residues (designated "CPB" in Scheme C). Thiol-reactive groups are shown below (PDT, variant 1, or maleimido, variants 2 and 3) were attached to another 10-20 mol % of polyallylamine (PAA) links (m=0.1n to 0.2n). The value of n is typically at least 50, and typically at most 2000 or at most 1000. The inventors have used two commercially available variants of PAA in the synthesis of CPB: one with n≈100 and another with n≈500, and values within this range are the ones most typically used for purposes of the invention.

The values of k, m and n-k-m are each non-zero fractions of n. Values of k generally will be in a range from 0.1n to 0.2n, and for m the range will typically be from 0.1n to 0.3n. Generally, k is about 0.2n and m is about 0.1n to 0.2n.

The inventors used a spacer derived from N-succinimidyl 3-(2-pyridyldithio)propionate to attach PDT groups and two variants of spacers for the maleimide group attachment: the linear aliphatic spacer derived from N-succinimidyl 6-maleimidocaproate (variant 2) and the cycloaliphatic spacer derived from N-succinimidyl trans-4-maleimidomethylcyclohexanecarboxylate (variant 3). The inventors have found that the cyclohexane ring of the latter compound significantly enhances the stability of CPB towards spontaneous cross-linking. CPB polymers according to the invention may also contain mixtures of the above-mentioned thiol-reactive groups in the same polymeric molecule. Single CPB polymers or mixtures of different ones may be used for purposes of the invention.

Scheme C. CPB: PAA-based thiol-reactive polymers with cholesteryl residues

A: Z = —(CH$_2$)$_2$—COOH  B: Z = —(CH$_2$)$_5$—$\overset{\oplus}{N}$Me$_3$$\overset{\ominus}{Br}$ Su = N-succinimidyl; Chol = β-cholesteryl The ionogenic groups (variant A and/or B in Scheme C, above) on the rest of the PAA links (65-70 mol %) were incorporated to confer water solubility to the CPB polymers, which allowed the use of aqueous media for the ANGIOFLEX™ modifications and avoiding the use of organic solvents. CPB polymers according to the invention may also contain mixtures of the above-mentioned ionogenic groups, either in the same polymeric molecule or in separate molecules.

EXAMPLES

Preparation of PBPC

Thus, the photo-reactive polymeric cross-linker PBPC was synthesized and characterized as described by Chorny et al., Adenoviral gene vector tethering to nanoparticle surfaces results in receptor-independent cell entry and increased transgene expression, Mol Ther 2006, 14:382-391, incorporated herein by reference. Briefly, PAA hydrochloride (M$_n$≈10 kDa, Sigma-Aldrich) was transformed into PAA base by treatment with Dowex G-55 (OH-form). The base in 2-propanol —CH$_2$Cl$_2$ was reacted at 0° C. with a mixture of N-succinimidyl 4-benzoylbenzoate and N-succinimidyl 3-(2-pyridyldithio)propionate (SPDP), added dropwise in a CH$_2$Cl$_2$-solution. The amounts of the active esters were chosen to be insufficient for the complete acylation of PAA amino groups, and the unreacted amino groups were then transformed into carboxylic groups by reaction with an excess of succinic anhydride. To quantify the amounts of PBPC bound to the ANGIOFLEX™ surface, some batches of PBPC were labeled with a suitable fluorescent probe (BODIPY FL), added as a commercially available amino-reactive form BODIPY FL SE (Invitrogen, Eugene, Oreg.) into the reaction mixture in the course of synthesis together with the other active esters. The label was attached to less than 0.5 mol % of PAA amino groups (less than 0.8% by weight), causing no noticeable influence on the solubility and chemical properties of PBPC. Because the fluorescence of BODIPY fluorophores is almost independent of the ANGIOFLEX™ background, the inventors were able to determine the amounts of PBPC on the ANGIOFLEX™ surface by comparing the fluorescence of ANGIOFLEX™ films treated with the labeled PBPC with this of PBPC solutions containing known amounts of the labeled polymer.

Preparation of PBPC-A

The photo-reactive polymeric cross-linker PBPC-A was synthesized and characterized similarly to PBPC. Briefly, PAA hydrochloride (M$_n$≈10 kDa, Sigma-Aldrich) was transformed into PAA base by treatment with Dowex G-55 (OH-form). The base in 2-propanol —CH$_2$Cl$_2$ was reacted at 0° C. with a mixture of N-succinimidyl anthraquinone-2-carboxylate and N-succinimidyl 3-(2-pyridyldithio)propionate (SPDP). The amounts of the active esters were chosen insufficient for the complete acylation of PAA amino groups, and the unreacted amino groups were then transformed into carboxylic groups by reaction with an excess of succinic anhydride as shown below.

The amounts of the attached groups were similar to those in the foregoing PBPC example (k≈0.2n, m≈0.4n), and the properties of PBPC-A were similar. In general, typical ranges for k, m and n for PBPC-A polymers are the same as those described earlier herein for PBPC. Model experiments showed that the anthraquinone group is nearly four times as efficient a photo-cross-linker as the benzophenone group. Thus, the use of PBPC-A in place of PBPC is expected to allow attachment to polyurethane surfaces at a lower UV light exposure level.

Preparation of CPB

The methodology of CPB synthesis resembled that used for PBPC, with several CPB formulations being prepared. PAA base (from PAA hydrochloride with $M_w \approx 75$ kDa, Sigma-Aldrich) was reacted in 2-propanol —$CH_2Cl_2$ at 0° C. with a mixture of N-succinimidyl β-cholesteryloxyacetate and another succinimide ester containing also a thiol-reactive group, such as SPDP (variant 1 on the Scheme C), N-succinimidyl 6-maleimidocaproate (EMCS, variant 2) or N-succinimidyl trans-4-maleimidomethylcyclohexanecarboxylate (SMCC, variant 3) bifunctional cross-linkers. The excess amino groups of PAA were then reacted with either succinic anhydride or N-succinimidyl 6-trimethylammoniocaproate bromide, forming carboxylic (subvariant A) or quaternary ammonium (subvariant B) ionogenic groups correspondingly. About 20 mol % of allylamine repeat units were modified with cholesteryl residues (k=0.2n).

The CPB compositions described herein were created using 75 kDa PAA, and the PBPC formulations used 15 kDa PAA, but the invention is not limited to these molecular weights. PAA may be reacted in non-aqueous solvent systems simultaneously with different active N-hydroxysuccinimide esters, each containing one of 3 residues (cholesteryl, thiol-reactive and ionogenic) as shown in Scheme C. These acylating agents form stable amide bonds with the PAA amino groups, thus randomly inserting the corresponding groups into the PAA macromolecule. In the case of carboxylic ionogenic groups, anhydrides of 1,ω-dicarboxylic acids (succinic, glutaric or adipic) may be used as acylating agents instead of the corresponding N-hydroxysuccinimide esters. N-Succinimidyl cholesteryloxyacetate (Chol-OCH$_2$COOSu), which can be used to insert cholesteryl residues into CPB, may be prepared from cholesterol as shown in Scheme D.

Scheme D. Synthesis of N-succinimidyl cholesteryloxyacetate

-continued

Chol-OCH$_2$COOSu

SuOH = N-hydroxysuccinimide; DMAc = N,N-dimethylacetamide
EDC = 1-(3-dimethylaminopropyl)-3-ethylcarbodiimide hydrochloride To insert trimethylammonio groups into the cationic variants of CPB polymers, one can use the active ester N-succinimidyl 6-trimethylammoniocaproate bromide, which can be prepared as a pure crystalline compound from 6-bromocaproic acid, as shown in Scheme E.

Scheme E. Synthesis of N-succinimidyl 6-trimethylammoniocaproate bromide

DCC = 1,3-dicyclohexylcarbodiimide

Scheme C provides the basis of a nomenclature system to designate specific CPB polymers, wherein the type of thiol reactive group is indicated by a numeral (1, 2 or 3) and the type of ionogenic group is indicated by a letter (A or B). Accordingly, four CPB polymers (CPB-1A, CPB-2A, CPB-3A and CPB-1B) were synthesized and characterized by $^1$H NMR. Some batches of CPB also contained a fluorescent label (BODIPY 564/570, attached as described above for labeling PBPC), to enable quantification of the polymer bound to the ANGIOFLEX™ surface.

Photoactivation of Polyurethane Surfaces with PBPC

Photoactivation with PBPC was carried out as follows. PBPC was dissolved in water (1 mg/ml) containing KHCO$_3$ (0.67 mg/ml) and buffered to pH ca. 5 with KH$_2$PO$_4$ (23 mg/ml). ANGIOFLEX™ leaflets or films were exposed to an excess of PBPC solution in the dark for 30 to 40 minutes (forming an adsorption layer of PBPC), and then exposed to UV light using a BioRAD UV Transilluminator 2000 in the analytical exposure. UV exposure was carried out for 15 minutes on each side of the film or leaflet, followed by a 20 minute exposure to the KHCO$_3$ buffer, and exhaustive washing in double distilled water. The ANGIOFLEX™ materials were then stored under sterile conditions overnight at 4° C. prior to reactions with CPB.

Cholesterol Modification of the Thiolated Polyurethane Surface

The reaction of CPB solutions with the surface-thiolated ANGIOFLEX™ resulted in a rapid formation of a stable interlocked network, thus binding cholesteryl residues onto the ANGIOFLEX™ surface with multiple covalent bonds (Scheme F). Solutions of CPB (1 mg/mL) in water—methanol having a pH close to 7 (for the anionic CPB, variant A, addition of choline bicarbonate as a base was required) were reacted at room temperature with ANGIOFLEX™ films that had been surface-modified with PBPC under UV-irradiation (as described above) and freshly reduced with TCEP.

Figure 1:
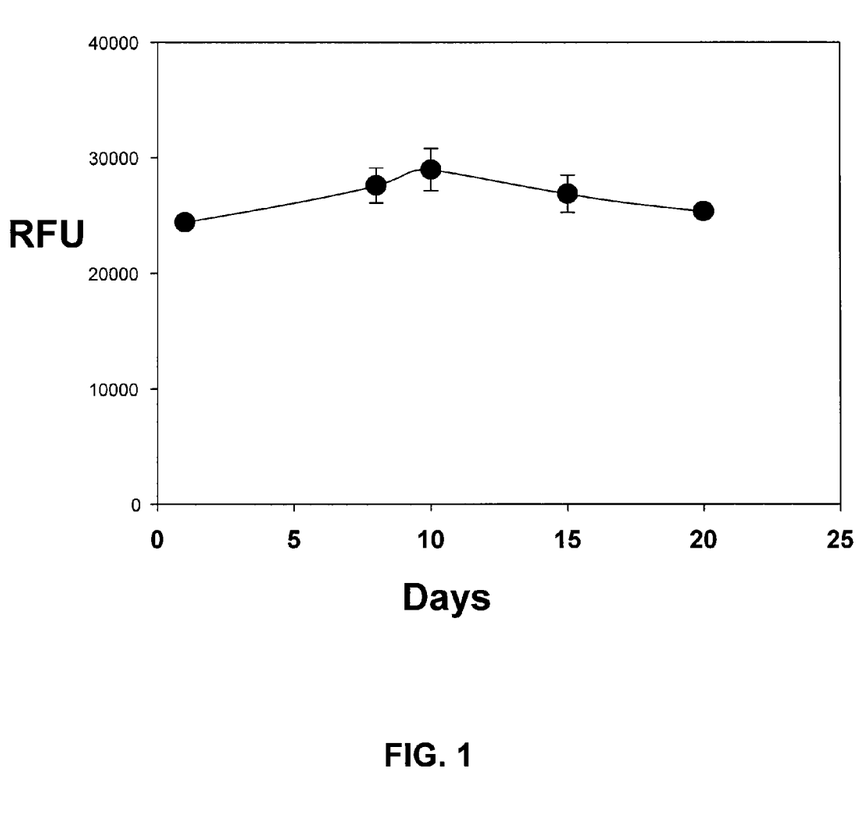
FIG. 1 is a plot showing the stability of BODIPY-labeled PBPC-CPB-2A binding to the surface of ANGIOFLEX™ films according to the invention, over 3 weeks.

Scheme F. Modification of thiolated ANGIOFLEX™ (polyurethane) with cholesteryl residues Chol = cholesteryl residues of CPB
L = binding bridge formed from SH and the thiol-reactive group of CPB Level of Binding and Stability of PBPC-CPB on ANGIOFLEX™ Surfaces Using the procedures described above, BODIPY-labeled CPB-2A was reacted with PBPC activated ANGIOFLEX™ films. The surface binding was quantitated with fluorometry, and then sample films were incubated under both physiologic and perfect sink conditions over time (FIG. 1). These data demonstrate ca. 2.0 nanomoles of cholesterol binding capability per cm$^2$ of ANGIOFLEX™ film. This level of surface bound cholesterol is comparable to that present in previously reported polyurethanes that were bulk modified with as reported by Stachelek et al., noted above. The fluorometry readings also showed stability of the binding over time (21 days) thus supporting the view that a cholesterol derivatized ANGIOFLEX™ surface will persistently interact to promote BOEC adhesion. The inventors are unaware of any previous experimental or clinical demonstration of persistent endothelial seeding such as shown here, and this is expected to provide substantial benefit for valve replacements, especially left side valve replacements.

PBPC-CPB Scanning Electron Microscopy (SEM) Results and Uniaxial Testing

These data confirmed that PBPC-CPB-2A modified ANGIOFLEX™ resulted in uniformly smooth surfaces that did not differ in terms of surface morphology from unmodified ANGIOFLEX™ (data not shown). Furthermore, uniaxial testing results demonstrated no detectable differences between PBPC-CPB modified versus unmodified ANGIOFLEX™ (Table 1). In these uniaxial studies the inventors examined the effects of photo-active surface chemistry (PBPC-CPB) on the bulk mechanical properties of ANGIOF-LEX™ specimens. Three groups were tested: Control, PBPC-CPB-1A, and PBPC-CPB-2A (see Scheme C). Each group consisted of 5 samples of 10 mm by 2 mm rectangular strips (5:1 ratio). A Universal Testing Machine (MTS Tytron 250 Microforce Testing System) was used, with each specimen conditioned at 10 mm/min at 30% of the initial specimen length for 5 cycles then loaded to failure at 10 mm/min. Data acquisition of force, displacement, and time was acquired at a sampling rate of 30 Hz. For each of the individual specimens the ultimate stress, ultimate stretch, tangent moduli with associate transition strain, total work and toughness was computed. All specimens' mechanical properties are reported as mean and standard error. A one-way ANOVA for each dependent variable as a function of treatment (control, anionic, cationic) was performed to assess whether significant differences existed in mechanical properties. Test results indicated that all three groups demonstrated the "classic" non-linear elastomer tensile response (data not shown). Moreover, there were no significant differences in material properties between the different surface treatments. Table 1 shows data comparing the mechanical properties of a control unmodified ANGIOFLEX™ polyurethane with ANGIOFLEX™ treated with two surface modifications according to the invention. The data reported include ultimate stress and strain, total work and toughness.

| Group | Ultimate Stress & Strain | | $W_{total}$ | $T_{total}(mJ/m^3)$ |
|---|---|---|---|---|
| | e | σ | | |
| Control | 4.18 ± 0.75 | 10.15 ± 2.42 | 82 ± 22 | 264 ± 78 |
| PBPC-CPB-1A | 4.99 ± 0.42 | 9.8 ± 0.9 | 76 ± 4 | 251 ± 13 |
| PBPC-CPB-2A | 4.59 ± 0.63 | 8.5 ± 2.2 | 73 ± 20 | 240 ± 68 |

All values reported in Table 1 are reported as mean±SD where n=5 per group. It is noteworthy that there were no statistical differences between groups in any measured parameter. Thus, the bulk mechanical properties of the polyurethane were retained after surface modification.

Ovine BOEC Attachment

Figure 2:
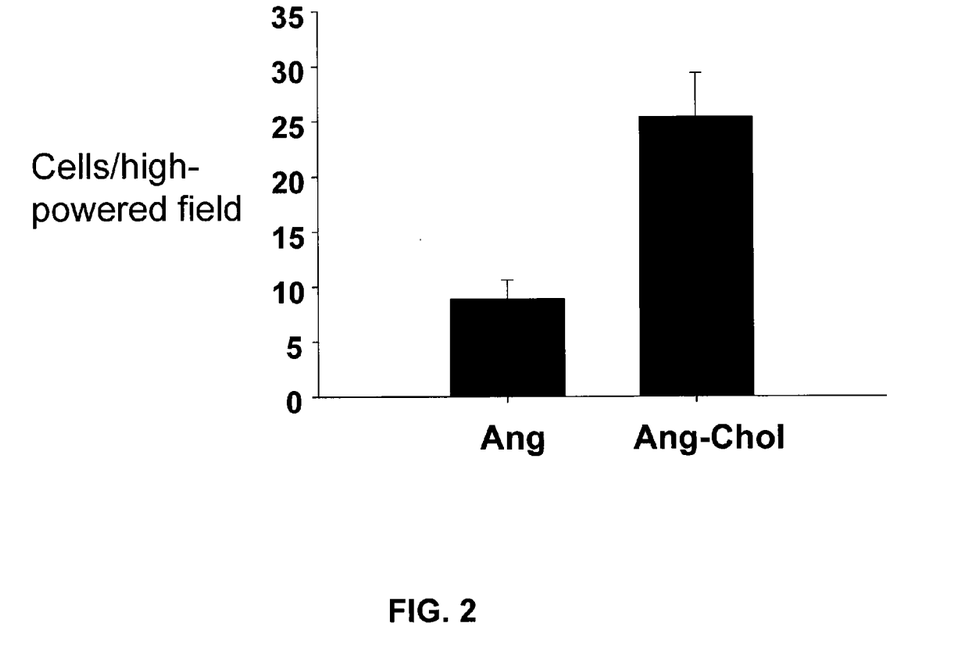
FIG. 2 shows data comparing attachment of ovine blood outgrowth endothelial cells (BOEC) to an ANGIOFLEX™ surface modified with PBPC-CPB-2A according to the invention with that of unmodified ANGIOFLEX™.

BOEC attachment over a 30 minute time period was compared for ANGIOFLEX™ with and without surface modification with photo-activated PBPC-CPB-2A (Scheme C). As shown in FIG. 2, ANGIOFLEX™ modified with PBPC-CPB-2A (Ang-Chol) demonstrated nearly three times the level of BOEC attachment (p<0.001) as unmodified ANGIOFLEX™ (Ang).

Ovine BOEC adhesion to ANGIOFLEX™ modified with PBPC-CPB-1A and -2A was also evaluated under high shear conditions. In these experiments the inventors used their published methodology (see Stachelek et al. references earlier herein) employing a FLEXCELL® Tension System (Flexcell International, Hillsborough, N.C.) with 2 hours of high shear flow (45 dynes/cm²) over BOEC seeded surfaces comparing two PBPC-CPB (1A and 2A, per Scheme C nomenclature) surface modified formulations. PCPB-CPB (-1A and -2A) and control slides were then seeded with 500,000 ovine BOECs and the cells were grown to confluence (2 days). The cells were then exposed to 45 dynes/cm² of laminar shear for 2 hours via the Flex Cell Streamer (Hillsborough N.C.) fluid flow delivery apparatus. Slides were washed in PBS and fixed in paraformaldehyde. Retained cells were photographed using phase contrast microscopy and stained with DAPI. Cells were quantified manually using fluorescent microscopy to quantify the number of DAPI positive cells.

Figure 3A:
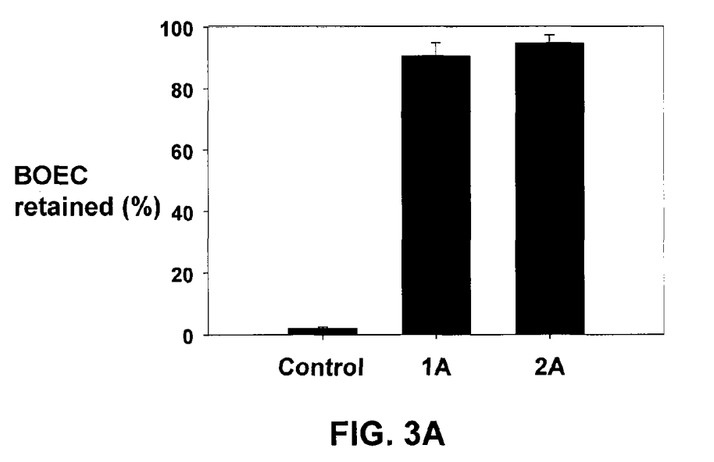
FIG. 3A shows data comparing adhesion of BOEC to surface modified ANGIOFLEX™ (PBPC-CPB-1A and -2A) according to the invention after 2 hours of shear with that of unmodified ANGIOFLEX™.
Figure 3B:
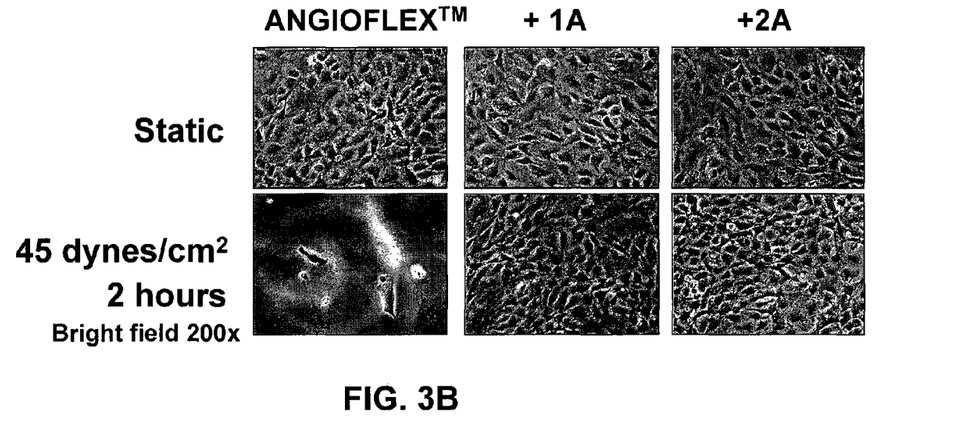
FIG. 3B shows photomicrographs depicting BOEC adhesion to surface modified and unmodified ANGIOFLEX™ under static conditions and after 2 hours of shear.

FIG. 3A shows data indicating that surface modified ANGIOFLEX™ according to the invention shows significantly greater (p<0.001) BOEC adhesion after 2 hours than did unmodified ANGIOFLEX™. FIG. 3B shows photomicrographs of the surfaces exposed to shear and evaluated in FIG. 3A as well as these surfaces under static conditions prior to 45 dynes/cm² shear.

In this challenging assay, more than 90% of the BOEC remained adherent to both of the PBPC-CPB modified surfaces after shear, versus fewer than 5% with the unmodified ANGIOFLEX™. These data are comparable to published results (Stachelek et. al, cited earlier herein) for a polyurethane that was bulk modified (not surface modified) with cholesterol and that had approximately the same level of surface cholesterol as the PBPC-CPB modified ANGIOFLEX™ samples in FIGS. 3A and 3B. Thus, adhesion was very good for ANGIOFLEX™ surfaces modified with PBPC-CPB according to the invention, and in contrast, there was little or no adhesion to unmodified ANGIOFLEX™.

Cell seeding of completely assembled polymer valves is possible prior to use in vivo but after formation of the completely assembled valves, via the methods and compositions of this invention. Thus, no changes in valve fabrication or assembly procedures are required for manufacture.

Although the invention is illustrated and described herein with reference to specific embodiments, the invention is not intended to be limited to the details shown. Rather, various modifications may be made in the details within the scope and range of equivalents of the claims without departing from the invention.

What is claimed:

1. A polymer according to structure I wherein Y is a thiol-reactive group selected from one or more of the following moieties and Z is an ionogenic group selected from one or more of the following moieties and wherein n is an integer and k, m and n-k-m are each non-zero fractions of n.

2. The polymer of claim 1, wherein Z is —$(CH_2)_2$—COOH.

3. The polymer of claim 1, wherein Z is

4. The polymer of claim 1, wherein Y is

5. The polymer of claim 1, wherein Y is

6. The polymer of claim 1, wherein Y is

7. A method of modifying the surface of a polymeric substrate, comprising contacting the surface of the polymeric substrate with a polymer according to structure II and/or a polymer according to structure III wherein n is an integer and k, m and n-k-m are each non-zero fractions of n; and exposing the surface to ultraviolet light;

further comprising subsequently converting the moieties to —$(CH_2)_2$—SH moieties and then contacting the surface of the substrate with one or more polymers according to structure I

I wherein Y is a thiol-reactive group selected from one or more of the following moieties and Z is an ionogenic group selected from one or more of the following moieties wherein n is an integer and k, m and n-k-m are each non-zero fractions of n; under conditions sufficient to cause reaction of the —$(CH_2)_2$—SH moieties with the thiol-reactive groups.

8. The method of claim 7, wherein the polymeric substrate is a polyurethane substrate.

9. The method of claim 7, wherein the polymeric substrate is a polyether polyurethane substrate.

10. A surface-modified polyurethane substrate prepared by the method of claim 9.

11. The surface-modified polyurethane substrate of claim 10, wherein the polyurethane substrate is a heart valve.

12. The surface-modified polyurethane substrate of claim 11, wherein the surface of the polyurethane substrate is contacted with the polymer according to structure II.

13. A polymer according to structure III

III wherein n is an integer and k, m and n-k-m are each non-zero fractions of n.

14. A method of modifying the surface of a polymeric substrate, comprising contacting the surface of the polymeric substrate with the polymer of claim 13 and exposing the surface to ultraviolet light.

15. The surface-modified polyurethane substrate of claim 11, wherein the surface of the polyurethane substrate is contacted with the polymer according to structure III.

* * * * *

UNITED STATES PATENT AND TRADEMARK OFFICE
CERTIFICATE OF CORRECTION

PATENT NO.         : 8,618,242 B2                                          Page 1 of 1
APPLICATION NO. : 13/263244
DATED              : December 31, 2013
INVENTOR(S)       : Levy et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 154 days.

Signed and Sealed this
Twenty-second Day of September, 2015

Michelle K. Lee
*Director of the United States Patent and Trademark Office*